United States Patent [19]

Demole

[11] 4,014,350
[45] Mar. 29, 1977

[54] AROMATIC COMPOSITIONS

[75] Inventor: Edouard Demole, Geneva, Switzerland

[73] Assignee: Firmenich S.A., Geneva, Switzerland

[22] Filed: June 12, 1975

[21] Appl. No.: 586,386

Related U.S. Application Data

[62] Division of Ser. No. 482,776, June 24, 1974, Pat. No. 3,920,027, which is a division of Ser. No. 219,136, Jan. 19, 1972, Pat. No. 3,840,023.

[30] Foreign Application Priority Data

Jan. 19, 1971 Switzerland .......................... 773/71
June 23, 1971 Switzerland .......................... 9156/71
Jan. 11, 1972 Switzerland .......................... 380/72

[52] U.S. Cl. .............................. 131/17 R; 131/144
[51] Int. Cl.$^2$ ............................................ A24B 15/00
[58] Field of Search ....................... 131/17, 144, 2; 426/175; 260/586

[56] References Cited

UNITED STATES PATENTS

| | | | |
|---|---|---|---|
| 3,380,456 | 4/1968 | Roberts et al. | 131/17 R |
| 3,840,023 | 1/1972 | Demole | 131/17 R |

Primary Examiner—Robert W. Michell
Assistant Examiner—V. Millin
Attorney, Agent, or Firm—Pennie & Edmonds

[57] ABSTRACT

Various compounds are disclosed to be useful in the flavoring of tobacco products. Many of said compounds are also useful as odoriferous ingredients and/or as flavoring agents in general for foodstuffs, beverages and pharmaceutical preparations.

3 Claims, No Drawings

AROMATIC COMPOSITIONS

This is a divisional of application Ser. No. 482,776, which was filed on June 24, 1974 now U.S. Pat. No. 3,920,027, which in turn was a divisional of application Ser. No. 219,136, which was filed on Jan. 19, 1972 now U.S. Pat. No. 3,840,023.

DESCRIPTION OF THE INVENTION

The present invention relates to compositions and a process for improving, enhancing or modifying the flavouring properties of foodstuffs, feedstuffs, beverages, pharmaceutical preparations and, more particularly, tobacco products.

It is well known that tobacco used for the preparation of cigarettes, for example, is composed essentially of a mixture of different types of tobacco which gives the characteristic flavour and aroma that is desired in the tobacco smoke produced. Thus, cigarettes currently manufactured usually contain mixtures of Virginia, Maryland or Kentucky tobacco in coordination with oriental or turkish tobacco.

The respective proportions of the various types of tobacco are varied in order to obtain the particular flavour and aroma desired. It is also common practice to employ flavouring substances and humectants as additives to these tobacco mixtures to further enhance the organoleptic properties thereof.

Accordingly, it is an object of the present invention to provide a process for improving, enhancing or modifying the organoleptic properties of a tobacco product by incorporating therein an aromatic composition or certain synthetic flavouring agents.

In accordance with one preferred embodiment of the present invention, the flavour and aroma of tobacco smoke is improved by adding to the tobacco (which may be natural tobacco or a tobacco substitute of natural or synthetic origin) a flavouring composition containing at least one compound selected from the following groups:

1. Amides of formula

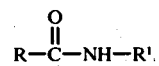

I wherein R and R¹ represent an alkyl radial comprising 1 to 6 carbon atoms, or a hydrogen atom.

Specific examples of the compounds comprised by formula I include:

| a) | N-isoamylacetamide | Ber., 58, 2017 (1925) |
| b) | N-isoamylformamide | Compt. rend., 176, 1159 (1923) |

2. Cycloaliphatic derivatives:

| a) | 3,5,5-trimethyl-cyclohex-2-en-4-ol-1-one | Tetrahedron, Suppl. 8, Part I, p. 1 (1966) |
| b) | 3,5,5-trimethyl-2,3-epoxy-cyclohexane-1,4-dione | n.c. |
| c) | 2,6,6-trimethyl-cyclohex-2-en-4-ol-1-one | n.c. |
| d) | 4,4,6-trimethyl-cyclohexa-2,5-dien-2-ol-1-one | n.c. |
| e) | 3,5,5-trimethyl-cyclohex-3-en-1-yl acetate | n.c. |
| f) | 3,5,5-trimethyl-4-hydroxy-4-[but-1-en-3-one]-cyclohex-2-en-1-one | J.Org.Chem., 33, 3566 (1968) |
| g) | 3,5,5-trimethyl-2-hydroxy-cyclohex-2-ene-1,4-dione | Phytochemistry, 10, 2755 (1971) |
| h) | 3,5,5-trimethyl-cyclohex-2-en-2-ol-1-one | J.Org.Chem. 24, 719 (1966) |

3. Phenol derivatives:

| a) | 2-hydroxy-5-methyl-acetophenone | c.a. |
| b) | 2-methyl-5-isopropenyl-anisole | Helv. Chim. Acta, 48, 1057 (1965) |

4. Heterocyclic ketones of formula

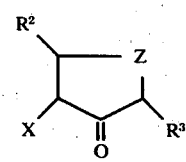

II containing a double bond in one of the position indicated by the dotted lines, and wherein X represents either a hydrogen atom or a hydroxyl group when the double bond is in the ring, or an oxygen atom when the double bond is external to the ring, $R^2$ and $R^3$ represent a lower alkyl substituent, and Z stands for oxygen or sulphur.

Specific examples of compounds comprised by the above indicated formula include:

| a) | 2,5-dimethyl-4,5-dihydrofuran-3-ol-4-one | Swiss patent No. 474,500 |
| b) | 2,5-dimethyl-4,5-dihydrothiophen-3-ol-4-one | D.O.S. No. 1,932,800 |
| c) | 2-methyl-5-ethyl-4,5-dihydrofuran-3-ol-4-one | Swiss patent No. 491,904 |
| d) | 2-ethyl-5-methyl-4,5-dihydrofuran-3-ol-4-one | Swiss patent No. 491,904 |

| | |
|---|---|
| e) 2,5-dimethyl-2,3-dihydrofuran-3-one | Helv. Chim.Acta,46,1259(1963) |

5. Caryophyllene derivatives:
a. caryophyllenepoxide of formula

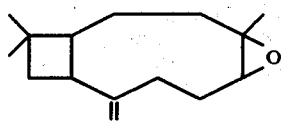

Helv. Chim. Actea, 51, 494(1968)
b. and c) caryophyllene alcohols of formula

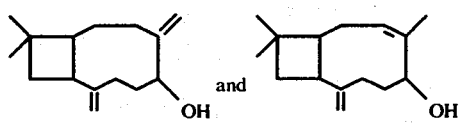

Helv. Chim. Acta, 51, 494 (1968)
6. Miscellaneous

| | |
|---|---|
| a) epoxy-β-ionone | Helv.Chim.Acta,29,1829 (1946) |
| b) 6-methyl-hepta-3,5-dien-2-one | USSR patent No. 138,612 |
| c) 3-isopropyl-cyclopent-2-en-1-one | J.Org.Chem., 33, 1656 (1968) |
| d) octa-3,5-dien-2-one | Belgian patent No. 660,099 |
| e) nonane-2,5,8-trione | Ber., 76, 183 (1943) |
| f) 2-methyl-5-(α-methyl-α-hydroxy-ethyl)-cyclohex-2-en-1-one | Ber., 38, 1719 (1905) |
| g) 4-methylthiobutan-2-one | C.A., 52, 9141e (1958) |

In the hereinabove list of compounds of the groups 1 to 6, immediately following the chemical name of each member there is given the commercial source or a literature reference giving a method for its preparation. Commercially available products are identified by the abbreviation c.a., and may be obtained from FLUKA A. G., Buchs S. G., Switzerland; ALDRICH CHEM. Co., Milwankee, Wis.; or K. & K. LABORATORIES INC., Mainview, N.Y. 11803.

In those instances wherein new compounds are described a detailed method of preparation is given in the course of this description or in one of the examples. New compounds are identified by the abbreviation n.c.

The results of the organoleptic evaluation tests are set out in the specific examples.

An additional object of the present invention is to provide compositions for flavouring tobacco or tobacco substitutes comprising at least one compound selected from the groups listed above.

The compounds listed above have been divided into groups based more on similarities of their chemical structure than on their specific organoleptic properties.

The wide range of organoleptic properties associated with the compounds described above makes it possible to achieve a variety of effects depending on the nature of the individual components used in a given aromatic mixture.

The compounds and/or flavouring compositions described herein may be used in a variety of forms. It is preferable, however, to utilize these compounds or compositions in the form of solutions thereof. The chemical nature, solubility and stability determine the form in which a given compound or composition is to be employed.

A convenient method for flavouring tobacco consists in spraying the tobacco with an alcoholic solution of the compound or flavouring mixture. Combinations of solvents such as alcohol and propylene glycol may also be used.

The proportions of the new compounds to be used in said compositions or in accordance with the process of the present invention can vary within wide limits. Said proportions depend particularly on the specific organoleptic effects it is desired to achieve and on the origin of the tobacco products to which the mentioned flavouring ingredients are added. For instance, interesting flavouring effects can be achieved with amounts ranging from 1 to 1000 ppm, based on the weight of the product flavoured. However, special effects may be achieved by proportions as high as 5 or even 10%. Typically, proportions comprised in between about 10 and 200 ppm are preferably used.

In all cases, the ranges given above may be varied, depending upon the specific odoriferous or flavouring effect it is desired to achieve.

A further object of the present invention is to provide a process for the preparation of a new cyclic ketone, the 4,4,6-trimethyl-cyclohexa-2,5-dien-2-ol-1-one. The process in accordance with the invention comprises treating isophorone with a halogenating agent, such as for example N-bromosuccinimide, to afford a 3,5,5-trimethyl-4-halocyclohex-2-en-1-one, and oxidizing the ketone thus obtained by means of a tertiary amine oxide, such as trimethylamine oxide.

The above mentioned process is better illustrated by the following reaction scheme:

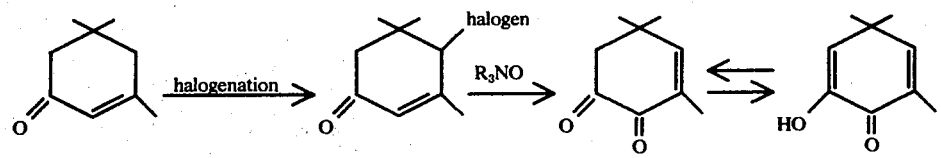

R = alkyl

The use of tertiary amine oxides for promoting the oxidation of haloderivatives is known and described in the chemical literature [see for example Berichte der Chemie, 94, 1360 (1961)]. In agreement with the prior art teachings, said oxidation was expected to proceed through a quaternary salt intermediate having the formula

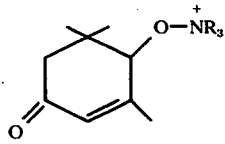

to yield as final product a cyclohexane-1,4-dione. We have unexpectedly found that by the oxidation of 3,5,5-trimethyl-4-halocyclohex-2-en-1-one, in accordance with the process of the present invention, a 1,2-dione derivative was formed instead. Said diketone was in equilibrium with its keto-enol form according to the above given scheme.

The present invention relates further to the new compounds which have been listed above.

Said compounds may be prepared in accordance with the methods described hereinbelow:

2. b. 3,5,5-Trimethyl-2,3-epoxy-cyclohexane-1,4-dione 2 ml of a 6N aqueous solution of NaOH have been added during a period of 15 minutes at 15° C to a mixture of 3,5,5-trimethyl-cyclohex-2-en-1,4-dione (3.7 g) and hydrogen hydroperoxide (8.3 ml of a 30 % solution) in 27 ml of methanol. The mixture was kept under stirring during 3 hours at 20°–25° C, treated with water and extracted with ether. The combined organic extracts were washed with water until neutrality, dried over $MgSO_4$ and evaporated. 3.33g (81.5%) of the desired product, b.p. 40° C/0.001 Torr, were thus obtained.

IR: 1715 cm$^{-1}$; MS: M$^+$= 168; m/e: 56 NMR (CCl$_4$): 1.05 (3H,s); 1.25 (3H,s); 1.50 (3H,s); 2.08 (1H,d, J=13 cps); 3.09 (1H,d, J=13 cps); 3.47 (1H,s) γ ppm.

3,5,5-Trimethyl-cyclohex-2-en-1,4-dione, used as starting material for the above described preparation, may be obtained in acordance with the procedure described in Tetrahedron, Suppl. 8, Part I, p. 1 (1966).

2. c. 2,6,6-Trimethyl-cyclohex-2-en-4-ol-1-one

Prepared in accordance with the procedure described in Tetrahedron, Suppl. 8, Part I, p. 1 (1966), starting from isophorone.

In addition to the ketal intermediate of formula

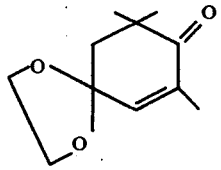 (a)

as described, we have obtained a ketal of formula

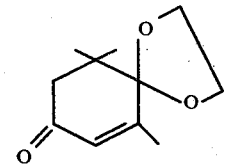 (b)

which has been separated by column chromatography on silicagel (elution: benzene + ethyl acetate).

Ketal (b) has been reduced by LiAlH$_4$ in ether solution and the product thus obtained directly hydrolysed in a mixture of dioxane and 5% H$_2$SO$_4$ at 20° C.

NMR (CCl$_4$): 1.10 (6H,s); 1.72 (3H,s); 1.85–2.40 (2H,m); 4.50 (2H, s broad); 6.64 (1H, s broad) γ ppm.

2. d. 4,4,6-Trimethyl-cyclohexa-2,5-dien-2-ol-1-one

Prepared according to Example 2.

2. e. 3,5,5-Trimethyl-cyclohex-3-en-1-yl acetate

Prepared by reduction by means of sodium borohydride in methanol of β-isophorone [obtained according to J. Am. Chem. Soc., 63, 2308 (1941)] and subsequent acetylation of the obtained 3,5,5-trimethyl-cyclohex-3-en-1-ol by means of acetic anhydride in the presence of sodium acetate at 50° C during 20 hours.

NMR (CCl$_4$): 1.0 (6H,s); 1.62 (3H,s); 1.92 (3H,s); 5.10 (1H,s); 4.6–5.2 (1H,m) γ ppm The invention also relates to a method for modifying, improving or enhancing the organoleptic properties of foodstuffs, feedstuffs, beverages and pharmaceutical preparations, which comprises adding to said materials a small but effective quantity of at least one compound selected from the class consisting of group 2 and the following group: 3,5,5-trimethyl-cyclohex-2-ene-1,4-dione, 2,2,6-trimethyl-cyclohexan-4-ol-1-one, 3,5,5-trimethyl-cyclohexan-4-ol-1-one, 3,5,5-trimethyl-4-methylene-cyclohex-2-en-1-one and 3,5,5-trimethyl-cyclohexane-1,4-dione. The preparation of the hereinabove mentioned compounds has been described in U.S. Pat. No. 3,380,456.

We have surprisingly found that whenever said compounds were incorporated to said materials or to flavouring compositions containing among their ingredients phenol or phenol derivatives, the harshness and the chemical character of their phenolic taste was reduced or even suppressed.

Such a finding is of great interest to the flavour industry, particularly for modifying the roasted character of the taste of certain beverages such as infusions or decoctions prepared from tea, coffee, lime-blossom tea. Moreover, their use is particularly interesting for the flavouring of meat, more specifically of smoked meat, of roasted cereals and roasted nuts. When taken separately, said compounds can also impart to the products to which they are added a caramel- or straw-like character and fine a useful application in the flavouring of infusions or decoctions and certain fermented foodstuffs in general.

The proportions previously indicated for tobacco flavouring equally apply for the use of the above compounds in accordance with the hereinabove described method. For the purpose of the present specification, the term "foodstuff" is used broadly; and it is deemed to indicate also products such as coffee, tea and cocoa.

The invention is better illustrated by the following examples.

EXAMPLE 1

7 g of a 1% alcoholic solution of 3,5,5-trimethyl-2,3-epoxy-cyclohexane-1,4-dione (in 95% ethyl alcohol) were sprayed onto a mixture of tobacco of "american blend" (100 g). The tobacco thus flavoured was used to manufacture "test" cigarettes, the smoke of which was then subjected to organoleptic evaluation by comparison with non flavoured cigarettes ("control"). The tobacco used to prepare the control cigarettes was preliminarily treated with 95% ethyl alcohol.

The panel of experts unanimously defined the taste of the test cigarettes as being sweeter than that of the control cigarettes; moreover, the smoke possessed a note with an improved herb-like character and was reminiscent of the taste of cigar smoke.

By following the same procedure as that given in above Example 1, other samples were evaluated. The hereinbelow table gives the list of the tested compounds as well as the quantities employed and the flavour observed.

nents of the clear filtrate, crude 3,5,5-trimethyl-4-bromo-cyclohex-2-en-1-one was obtained.

NMR (CCl$_4$): 1.16 (3H,s); 1.25 (3H,s); 2.11 (3H,s); 2.07 (1H,d, J=16 cps); 2.53 (1H,d, J=16 cps); 4.45 (1H,s); 5.78 (1H,s) $\gamma$ ppm.

b. During a period of 30 minutes 3,5,5-trimethyl-4-bromo-cyclohex-2-en-1-one (43.4 g) was added to a solution kept at 40° C of anhydrous trimethylamine N-oxide (32 g) in 100 ml of anhydrous chloroform. The reaction was slightly exothermic and the temperature of the mixture was kept at 45°–50° C by external cooling during the whole addition. After cooling to room temperature, said mixture was poured onto 110 ml of 10% H$_2$SO$_4$ and the organic layers which separated were washed with water (3 ×), a 10% solution of sodium carbonate (3 ×) and finally with water again (3 ×) until neutralisation.

By evaporation of the volatile components, and subsequent distillation of the resulting residue a product was obtained at b.p. 47°–60° C/0.001 Torr. This product was treated with petrol-ether (30°–50° C) and then successively washed with a 5% aqueous solution of sodium carbonate (2 ×) and a 2% aqueous solution of

TABLE

| Compound | Amount [g][1] | Organoleptic Evaluation[2] |
|---|---|---|
| 1. a) | 1.0 – 10.0 | Nutty, chocolate taste |
| 1. b) | 1.0 – 10.0 | Rich nutty taste; sweet flue-cured character; chocolate; adds body |
| 2. a) | 1.0 – 10.0 | Sweet, flue-cured character |
| 2. b) | " | Sweet, phenolic flue-cured character; some nutty chocolate taste |
| 2. c) | " | Flue-cured character; slight nutty, phenolic taste; some ionone character |
| 2. d) | 7.0 | Sweet, woody character; anise-like note; more pleasant |
| 2. e) | 1.0 – 10.0 | Sweet, woody, flue-cured character |
| 2. f) | 1.0 – 10.0[3] | Sweet, flue-cured character |
| 2. g) | 1.0 – 10.0 | Sweet, woody, herb-like |
| 2. h) | 1.0 – 10.0 | Sweet, herb-like |
| 3. a) | 1.0 – 10.0 | Rich sweet, nutty taste; adds flue-cured character |
| 3. b) | " | Phenolic taste; slight Burley effect |
| 4. a) | 0.5 | Sweet, slightly woody, caramel and honey-like |
| 4. b) | 1.0 | Fruity, woody, slightly sulphur-like |
| 4. c) | 1.0 – 5.0 | Sweet, caramel |
| 4. d) | " | Sweet, caramel |
| 4. d) | 0.1 – 0.5 | Caramel |
| 5. a) | 1.5 – 2.5 | Woody, cigar smoke-like; orient tobacco note |
| 5. b) and c) | 2.5 – 5.0 | as above |
| 6. a) | 1.0 | Sweet, nutty, chocolate taste; adds body; some flue-cured character |
| 6. b) | 10.0 | Sweet, nutty, chocolate taste; adds body |
| 6. c) | 10.0 | Sweet, green note |
| 6. d) | 10.0 | Adds body; flue-cured flavour note |
| 6. e) | 10.0 | Sweet, nutty, chocolate taste; some flue-cured character |
| 6. f) | 10.0 | Flue-cured character, phenolic; nutty, chocolate taste; adds body |
| 6. g) | 10.0 | Some Burley character |

[1]The amounts indicated refer to the quantities of a 1% alcoholic solution (95% ethyl alcohol)
[2]The characters given refer to specific flavour properties of the tested compounds on tobacco as compared with a non flavoured tobacco.
[3]The amount indicated refers to the quantities of a 2% alcoholic solution (95% ethyl alcohol).

EXAMPLE 2 a. A mixture of isophorone (13.82 g; 0.1 Mole) and N-bromo-succinimide (17.80 g; 0.1 Mole) in the presence of traces of $\alpha,\alpha'$-azodiisobutyronitrile was refluxed in 500 ml of CCl$_4$ during 15 minutes. 500 ml of petrol-ether (30°–50° C) were then added to the cool reaction mixture and the succinimide thus precipitated was filtered off. By evaporating the volatile compo- NaOH (5 ×). The mother liquors were acidified and immediately extracted with diethyl ether.

The combined extracts were washed, dried over MgSO$_4$ and evaporated at reduced pressure. 8 g of the desired product were thus obtained (95% purity). The subsequent purification was carried out by sublimation at 70°–80° C/10 Torr, and yielded 6 g of pure 4,4,6-trimethyl-cyclohexa-2,5-dien-2-ol-1-one. The product had a positive test when treated with a solution of ferric chloride (blue-violet colour); m.p. 46° C.

| | |
|---|---|
| IR (CCl$_4$) | : 1630, 1650, 3440 cm$^{-1}$ |
| UV | : $\lambda_{max}^{EtOH}$ = 205, 249, 310 m$\mu$ ($\epsilon$ = 5650, 7880, 2420 respectively) |
| MS | : M$^+$ = 152; m/e: 109 |
| NMR (CCl$_4$) | : 1.27 (6H,s); 1.92 (3H,s); 5.97 (1H, pseudo d, J = ca. 2.5 cps); 6.34 )1H, m); 6.65 (1H,m) $\delta$ ppm. |

Under the conditions used for carrying out the above given analysis, the compound showed a keto-enol structure represented by the following formula

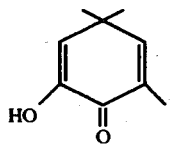

However, under other conditions it is reasonable to assume that the keto-enol equilibrium may be in favour of a diketonic structure according to the following equation:

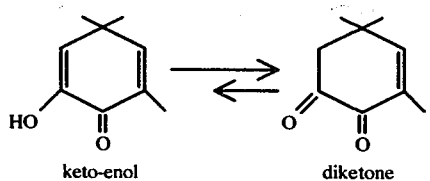

keto-enol     diketone

By replacing trimethylamine oxide by other tertiary aliphatic or cycloaliphatic amine oxides analogous results were achieved. Further, halogenating reagents other than N-bromo-succinimide, able to afford positive halogens, may be used for promoting the halogenation step.

EXAMPLE 3

The following flavouring compositions were prepared by admixing (parts by weight):

|  | A (control) | (test) B | C |
|---|---|---|---|
| p-ethylguaiacol 1 %* | 10 | 10 | 20 |
| guaiacol 1 %* | 15 | 15 | 30 |
| 3,5,5-trimethyl-cyclohexane-1,4-dione 10 %* | — | 30 | 30 |
| 95 % ethyl alcohol | 975 | 945 | 920 |
|  | 1000 | 1000 | 1000 |

*in 95 % ethyl alcohol

Flavours A, B and C were then compared in a concentration of 0.06 g of flavour for 60 ml of sugar syrup (prepared by dissolving 650 g of sucrose in 1350 ml of water).

The finished syrups were tested by a panel of qualified tasters who expressed their views on the value of the flavours used for their preparation. These persons declared unanimously that the taste of the syrup which had been flavoured with composition B had a more diffuse note than the syrup flavoured with compositon A; moreover, the typical phenolic character shown by this latter syrup was well masked. By using composition C, analogous results were obtained although less pronounced.

Flavours A, B and C were then compared in a concentration of 0.06 g of flavour for 60 ml of salt solution (prepared by dissolving 0.5 g of NaCl in 100 ml of water).

In this case also the flavour experts declared that the taste of the beverages which had been flavoured with compositions B and C lacked the phenolic character of the beverage flavoured with composition A.

EXAMPLE 4

The following flavouring compositions were prepared by admixing (parts by weight):

|  | A (control) | (test) B | C |
|---|---|---|---|
| p-ethyl phenol 1 %* | 10 | 10 | 20 |
| phenol 1 %* | 15 | 15 | 30 |
| 4,4,6-trimethyl-cyclohexa-2,5-dien-2-ol-1-one 10 %* | — | 30 | 30 |
| 95 % ethyl alcohol | 975 | 945 | 920 |
|  | 1000 | 1000 | 1000 |

*in 95 % ethyl alcohol

The above given flavours were then compared in a sugar syrup and in salt aqueous solution exactly as indicated in Example 3. The flavour experts declared that the taste of the beverages which had been flavoured with compositions B and C lacked the phenolic taste note of the beverages flavoured with composition A; the overall note was more rounded-off and possessed a better flavour harmony.

By replacing 4,4,6-trimethyl-cyclohexa-2,5-dien-2-ol-1-one by 3,5,5-trimethyl-2,3-epoxy-cyclohexane-1,4-dione, 2,6,6-trimethyl-cyclohex-2-en-4-ol-1-one, 3,5,5-trimethyl-cyclohex-3-en-1-yl acetate, 3,5,5-trimethyl-4-hydroxy-4-[but-1-en-3-one]-cyclohex-2-en-1-one, 3,5,5-trimethyl-cyclohex-2ene-1,4-dione, 3,5,5-trimethyl-cyclohex-2-en-4-ol-1-one, 2,2,6-trimethyl-cyclohexan-4-ol-1-one, 3,5,5-trimethyl-4-methylene-cyclohex-2-en-1-one, 3,5,5-trimethyl-2-hydroxy-cyclohex-2-ene-1,4-dione, 3,5,5-trimethylcyclohexan-4-ol-1-one, 3,5,5-trimethyl-cyclohexane-1,4-dione or 3,5,5-trimethyl-cyclohex-2-en-2-ol-1-one.

I claim:

1. A process for improving, enhancing or modifying the organoleptic properties of a tobacco product, which comprises adding thereto about 1 to about 1000 parts per million based on the weight of tobacco of at least one compound selected from the group consisting essentially of:

a. caryophyllenepoxide of formula

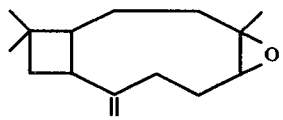

b. and c) caryophyllene alcohols of formula

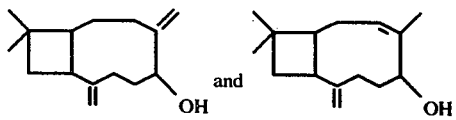

2. A tobacco or tobacco product having added thereto about 1 to about 1000 parts per million based on the weight of tobacco of at least one compound selected from the group consisting essentially of:

a. caryophyllenepoxide formula

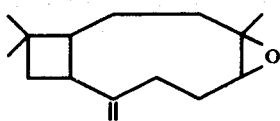
b. and c) caryophyllene alcohols of formula
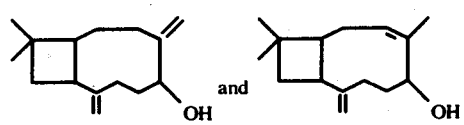
3. A tobacco flavouring composition which comprises at least one compound selected from the group consisting essentially of:
   a. caryophyllenepoxide of formula
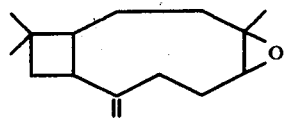
b. and c) caryophyllene alcohols of formula
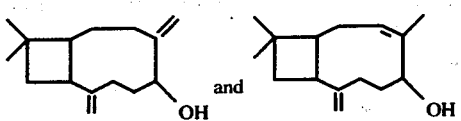
* * * * *

UNITED STATES PATENT AND TRADEMARK OFFICE
CERTIFICATE OF CORRECTION

PATENT NO. : 4,014,350
DATED : March 29, 1977
INVENTOR(S) : Edouard Demole

It is certified that error appears in the above-identified patent and that said Letters Patent are hereby corrected as shown below:

Column 2, lines 45-50, formula II, reads 

should read 

Column 7, lines 22-23, reads "flavour observed", should read --flavour effect observed--

Signed and Sealed this sixteenth Day of August 1977

[SEAL]

Attest:

RUTH C. MASON
*Attesting Officer*

C. MARSHALL DANN
*Commissioner of Patents and Trademarks*